United States Patent [19]
Ross, Jr. et al.

[11] Patent Number: 5,921,985
[45] Date of Patent: Jul. 13, 1999

[54] EXTERNAL FIXATION DEVICE AND METHOD

[75] Inventors: John David Ross, Jr., Ovilla; Robert D. Welch, Jr., Dallas, both of Tex.

[73] Assignee: Texas Scottish Rite Hospital, Dallas, Tex.

[21] Appl. No.: 09/021,711

[22] Filed: Feb. 10, 1998

[51] Int. Cl.[6] ................................................ A61B 17/64
[52] U.S. Cl. ............................................. 606/59; 606/54
[58] Field of Search ................................ 606/54, 55, 56, 606/57, 58, 59

[56] References Cited

U.S. PATENT DOCUMENTS

| | | |
|---|---|---|
| 2,372,866 | 4/1945 | Tofflemire . |
| 2,391,537 | 12/1945 | Anderson . |
| 2,391,693 | 12/1945 | Ettinger . |
| 2,393,694 | 1/1946 | Kirschner . |
| 4,220,146 | 9/1980 | Cloutier ..................................... 606/90 |
| 4,244,360 | 1/1981 | Dohogne . |
| 4,271,832 | 6/1981 | Evans et al. . |
| 4,745,913 | 5/1988 | Castaman et al. . |
| 4,890,631 | 1/1990 | Hardy ........................................ 606/59 |
| 5,047,029 | 9/1991 | Aebi et al. ................................ 606/61 |
| 5,334,203 | 8/1994 | Wagner ..................................... 606/61 |
| 5,451,225 | 9/1995 | Ross, Jr. et al. ........................... 606/59 |
| 5,545,167 | 8/1996 | Lin ............................................ 606/61 |
| 5,611,800 | 3/1997 | Davis et al. ............................... 606/61 |
| 5,624,440 | 4/1997 | Huebner .................................... 606/59 |
| 5,630,814 | 5/1997 | Ross, Jr. et al. ........................... 606/59 |
| 5,683,389 | 11/1997 | Orsak ........................................ 606/59 |

*Primary Examiner*—Michael Buiz
*Assistant Examiner*—David O. Reip
*Attorney, Agent, or Firm*—Vinson & Elkins L.L.P.

[57] ABSTRACT

An orthopedic fixation device and method are disclosed using circular rod stock and circular positive threaded fixation pins. The fixation pins are held in place relative to the fixation surface and relative to the rod by dual sectioned clamps which can be added to the rod at any time without regard to whether there are other clamps already in place at other locations along the rod. The clamps are held in place by a locking bolt which has a hole in a shank which allows the fixation pin to be inserted through the hole and into the fixation surface. The locking bolt contains a washer having a circular divot positioned in mating relationship with the inserted fixation pin. When the bolt is tightened, the clamp sections are forced together to grip the rod and also the divot portion of the washer is forced into contact with the fixation pin, thereby effectively reducing the circumference of the bolt hole which in turn provides three points of friction contact for maintaining the structure in rigid relationship.

17 Claims, 4 Drawing Sheets

5,921,985

EXTERNAL FIXATION DEVICE AND METHOD

TECHNICAL FIELD OF THE INVENTION

This invention relates generally to external fixation of orthopedic fractures, and more specifically to a clamp disposable on an external rod that enables continuing fixation at any point along the rod without disturbing existing fixation pins already installed.

BACKGROUND OF THE INVENTION

The use of external fixation devices in orthopedic procedures for holding bones in position relative to each other has now become common practice. Typically, such devices use a rod positioned parallel to the bones to be fixated and various fixation pins are mounted on the rod with one end of the pin being secured, usually by screw threads, to the bone. The shaft of the fixation pin is then attached on a semipermanent manner to the rod.

Several problems must be overcome in order to make such a system practical and useful. One of the problems is the weight of the total structure, and another problem is the fact that each fixation pin must be held rigid without slipping or breaking, even under stress, and must be capable of being positioned anywhere along the rod. The fixation pins must be able to be placed at various angles to the bone and must be able to be added or removed independently from all of the other devices connected to the rod. A further problem is that some of the fixation pins are connected to the bone by threads, which, if constructed by the traditional method of cutting the pin shank, would result in a weakened point on the shaft which is susceptible to breaking. Of course, one solution is to make the entire shank heavier. A more practical solution, however, is to use positive threads in which the thread bottoms (valleys) lie along the circumferential periphery of the pin so that the thread tops (ridges) actually have a circumference larger than the circumference of the shank.

Several patents have addressed this issue, particularly U.S. Pat. Nos. 4,745,913, 5,624,440 and 5,047,029. The '913 patent addresses these same issues and discloses a non-round bar for support of the fixation pin. The fact that the bar is not round prevents the pins mounted therealong from entering the fixation surface at selectably different angles. In addition, the mechanism of the '913 disclosure locks the fixation pins to the rod, in part, by a layer of deformable material 15' whose ability to provide continuous, repeatable and dependable grip on the pins is questionable.

The other prior art shows cumbersome arrangements which are both heavy and not very easy to use. Most such prior art arrangements require multiple locking screws for first mounting a clamp and then mounting the fixation pin.

Accordingly, there exists a need in the art for a fixation system that allows for the addition of one or more fixation pins even when other such pins, or other apparatus, is mounted to the rod and fixed to the fixation surface.

There is a further need in the art for such a device that allows for the insertion toward the fixation surface of positive threaded fixation pins without requiring the removal of other such fixation pins already in place.

There is a still further need in the art for a fixation pin holding bolt which can allow a multicircumferential pin to pass therethrough and then tightly grip the pin at three or more distinct points to support the pin without rotation.

A still further need exists in the art for a fixation device which allows for the easy placement of fixation pins therealong in any angle to the fixation surface and lockable with respect to rotational, longitudinal and distance with respect to the fixation surface.

SUMMARY OF THE INVENTION

These and other objects, features and technical advantages are achieved by a system and method which uses a circular rod having attachable thereto any number of clamps which clamps in turn control the positioning of fixation pins with respect to the fixation surface. Each clamp is constructed advantageously from a pair of mating sections, each such section advantageously having a substantially semicircular cutout such that when the dual sections are put together, the cutout surrounds the rod, and when the sections of the clamp are brought together, the clamp is frictionally connected to the rod in any rotational positioning around the rod desired.

The clamps, on one embodiment, are forced together by bolts spaced on opposing sides of the rod, one bolt being a traditional clamp bolt and the other bolt, advantageously the bolt closest to the fixation surface, containing a hole through which the positive threaded fixation pin can pass. The hole has a circumference larger than the circumference of the fixation pin, and the bolt has a washer which is positioned on the shank of the bolt and which has a circular divot with a radius smaller than that of the fixation pin in a top surface such that when the bolt is tightened against the clamp, the washer is forced to move toward the top surface of the bolt, and the edges of the divot on the washer engage a portion of the fixation pin, effectively reducing the size of the hole and providing a secure three point force on the pin to maintain it in position with respect to the fixation surface.

In operation, the rod can be in place and the clamp fitted over the rod. The distal bolt (or a hinge at the distal end of the clamp) serves to hold the distal end sections of the split clamp sections. The bolt having the hole therein is positioned in the proximal section of the clamp and when tightened serves to pull the two clamp sections together around the rod. Between the bolt head and the clamp, on the side of the clamp where the hole in the bolt is, the washer is positioned. The hole in the bolt is lined up with the fixation surface and a fixation pin is inserted through the hole and screwed or otherwise fastened to the fixation surface, such as a bone. When the fixation pin is in place, a nut on the opposite end from the bolt head is tightened, thereby locking the fixation pin to the clamp. At the same time the clamp is tightened to prevent rotation of the clamp around the rod and to prevent longitudinal displacement of the clamp along the rod.

The washer and the bolt are designed such that they will not rotate with respect to each other. The washer is advantageously constructed with increased friction contact so that the whole locking structure does not rotate with respect to the clamp.

One technical advantage of our invention is that any number of positive threaded fixation pins can be positioned in any order at any angle along a fixation surface.

A further technical advantage is that the clamp can be positioned with respect to the fixation surface and temporarily secured to achieve a secure grip on the rod. The fixation pin can then be inserted through the hole in the bolt and screwed into the fixation surface with the device thus being used as a guidance for precise alignment and placement of the fixation pin. Once the fixation pin is in place, the bolt may be tightened to lock the pin to the clamp and further secure the clamp to the rod.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

DESCRIPTION OF THE PREFERRED EMBODIMENTS

Figure 1:
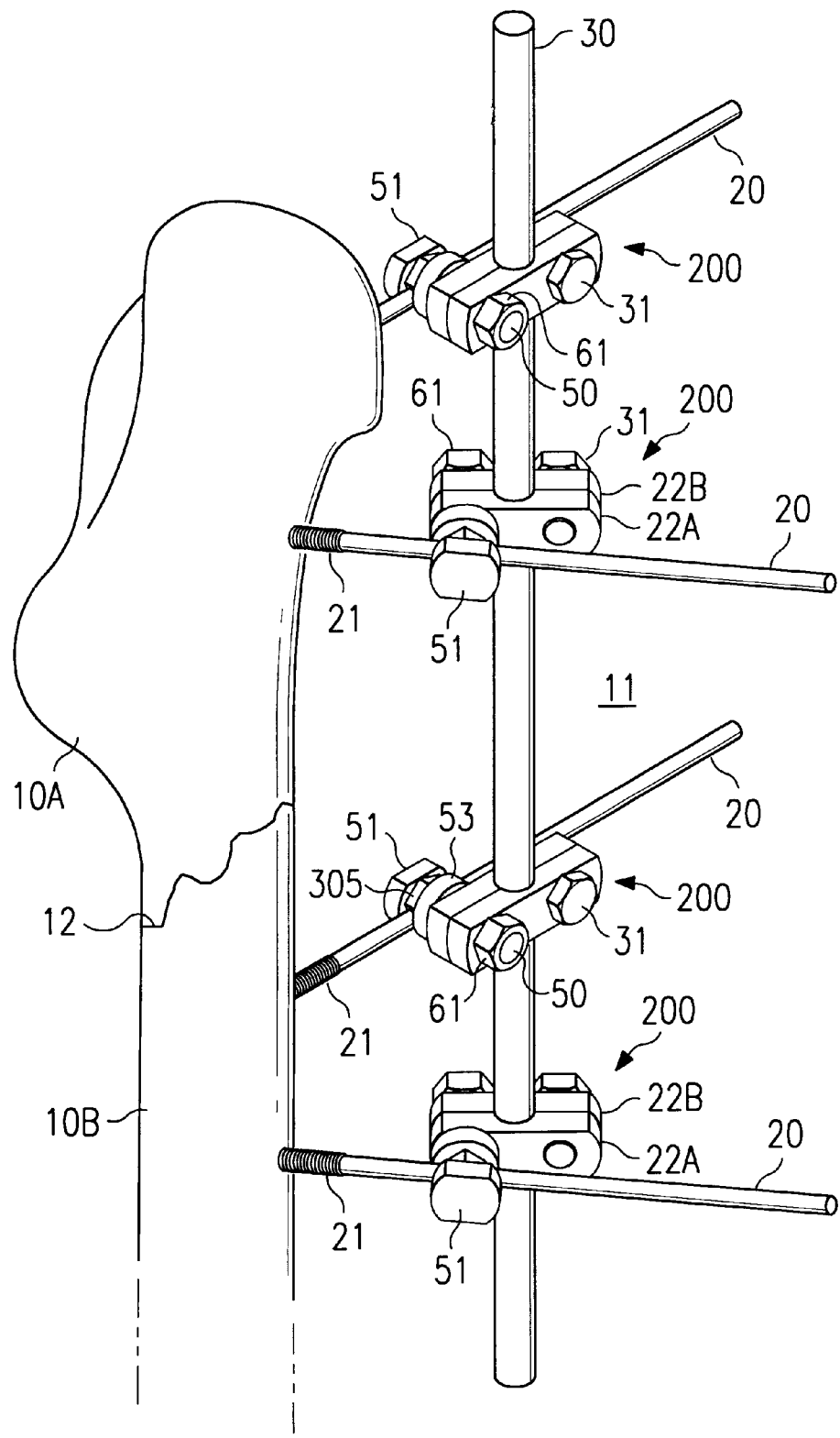
FIG. 1 is a general perspective view of the inventive clamp assemblies 200 in use during fixation.

FIG. 1 is a perspective view of a preferred embodiment of the inventive mechanism implemented as a fixation assembly 11. Fracture 12 separates bone pieces 10A and 10B. Fixation pins 20 are screwed (or otherwise driven) into bone pieces 10A and 10B via screw threads 21, and are secured to rod 30 by clamp assemblies 200. Fracture 12 may thus be secured to enable healing. One or more assemblies 11 can be positioned around bone 10A, 10B.

As shown on FIG. 1 and in greater detail in other views, fixation pins 20 advantageously (although not mandatorily) have positive profile threads 21 enhancing engagement on bone pieces 10A and 10B. Positive profile threads 21 allow the cross-sectional area of fixation pins 20 not to be diminished in the threaded portion, thus avoiding creation of a weak spot and enhancing fixation pin 20's resistance to breaking. Positive profile threads 21 cause the effective diameter of fixation pins 20 to be greater in the threaded portion than in the non-threaded portion. This, as discussed above, requires that hole 506 in member 50 (FIGS. 3 and 4) be larger than the diameter of the shank of fixation pin 20.

Figure 2:
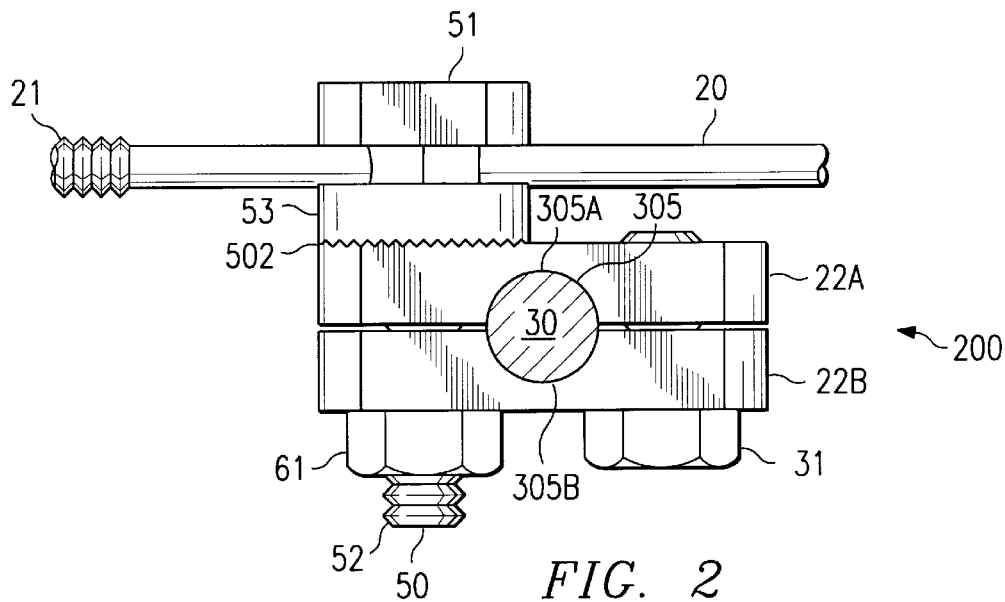
FIG. 2 illustrates the inventive clamp assembly as assembled.

Turning now to FIG. 2, clamp assembly 200 can be seen in more detail. In a preferred embodiment, clamp halves 22A and 22B are disposed either side of rod 30 and are secured by proximal member 50 and distal bolt 31 (the terms "proximal" and "distal" defined with reference to the bone on which fixation is to be performed). Substantially semicircular cutouts 305A and 305B in clamp halves 22A and 22B engage upon the outer surface of rod 30 forming a friction grip interface therebetween.

Figure 3:
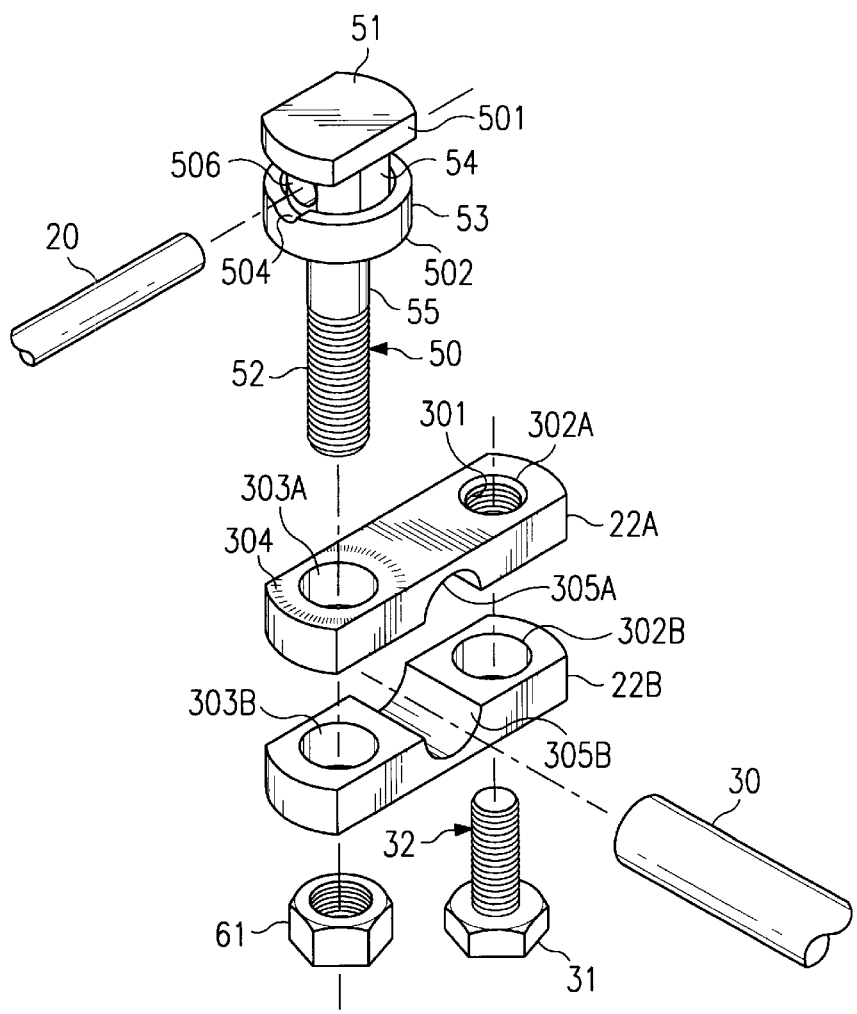
FIG. 3 is an exploded view of FIG. 2.
Figure 3A:
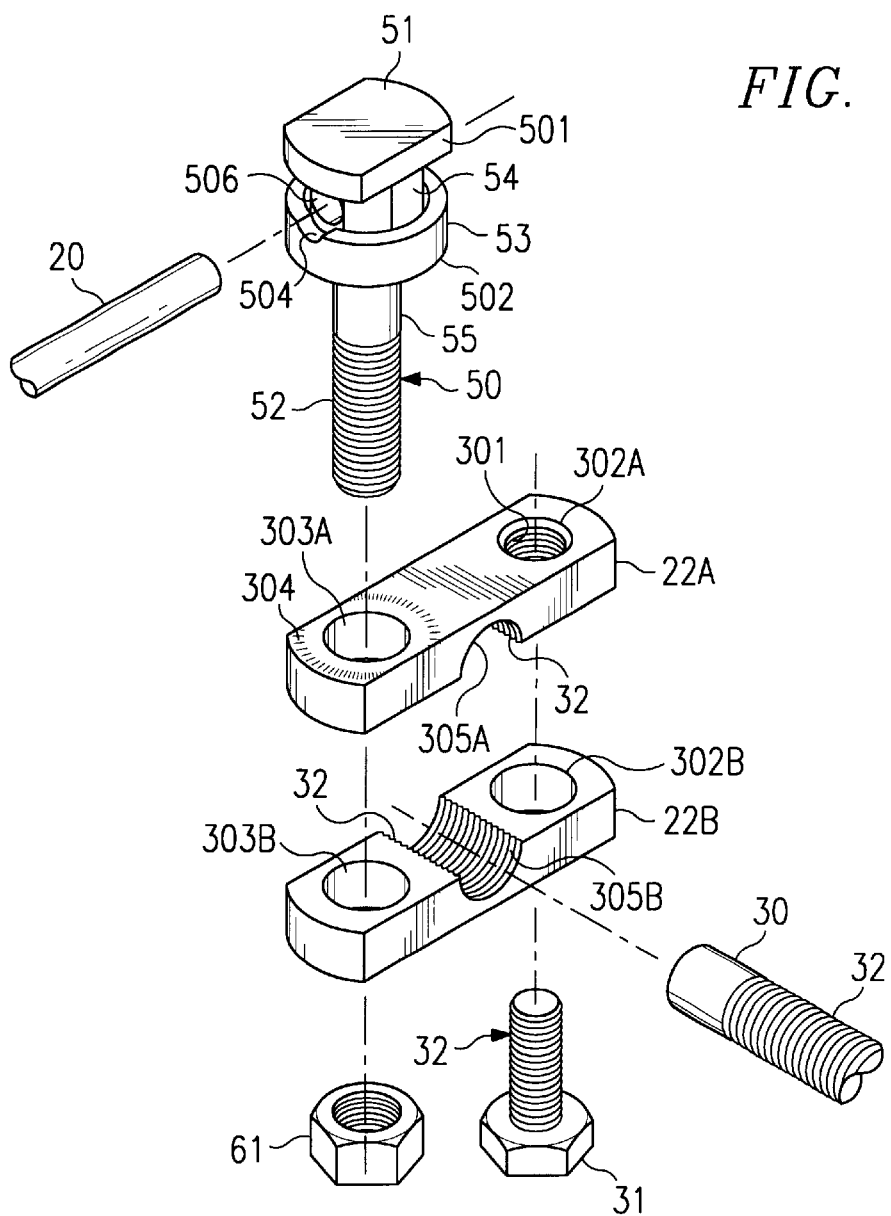
FIG. 3A illustrates an alternative embodiment providing mating threads 32 at the interface of rod 30 and semicircular clamp cutouts 305A and 305B.

In one embodiment, shown in FIG. 3, the engaging surfaces of rod 30 and semicircular cutouts 305A and 305B are plain. In another embodiment, shown in FIG. 3A, the corresponding engaging surfaces have mating threads 32. This permits selection of a threaded rod or stud as rod 30, whereby inventive clamp 200 may then be engaged thereon without damaging the threads 32 on rod 30. The threaded interface 32 between rod 30 and semicircular cutouts 305A and 305B as shown on FIG. 3A also provides improved rotational stability because of the intimacy of the fit in the threaded engagement (i.e. increased area of contact and wedging effect of threads clamped on thread). Longitudinal stability is further improved because of the interlocking feature of the threaded engagement. In application of the alternative embodiment illustrated in FIG. 3A, inventive clamp 200 is assembled on rod 30 at the desired point. Small changes in position are then accomplished by rotating assembled clamp 200 about rod 30 like a nut before inserting fixation pin 20.

Figure 6A:
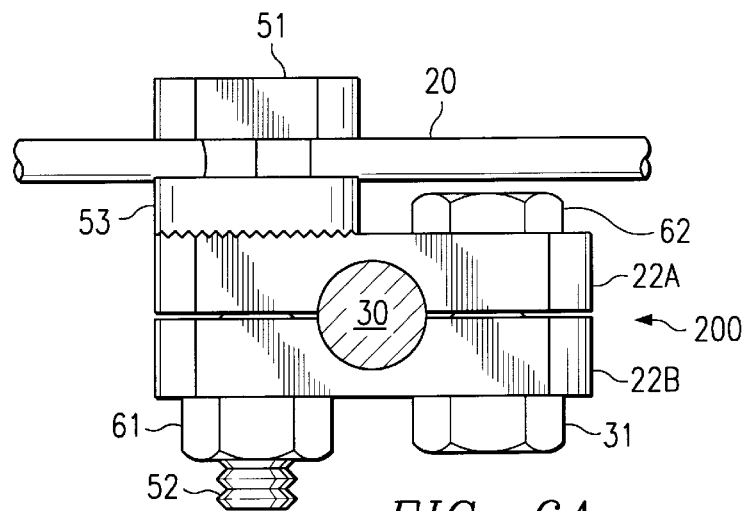
FIGS. 6A and 6B illustrate alternative embodiments in which clamp assembly 200 is secured at a distal end by nut 62 or hinge 62 respectively.
Figure 6B:
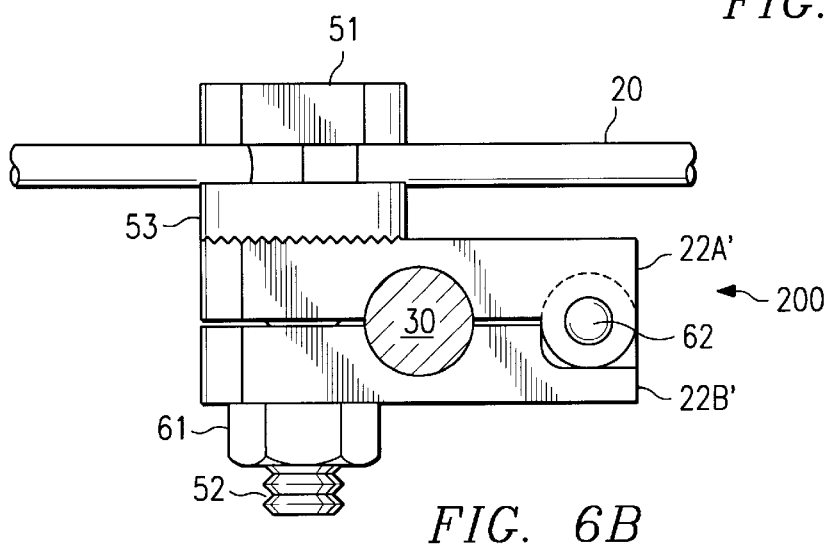

Returning now to FIG. 2, member 50 has threads 52 upon which nut 61 serves to tighten clamp 200 sections 22A and 22B together. Bolt 31 can either screw into section 22A, or, as will be discussed, can fasten to an external nut. Again, in a preferred embodiment, and with momentary reference to FIG. 3, distal bolt 31 secures clamp halves 22A and 22B by engagement upon internal threads 301. Other embodiments of the invention described below with reference to FIGS. 6A and 6B show alternatives to securing clamp halves 22A and 22B at the distal end.

With further reference to FIG. 2, it will be seen that in addition to securing the proximal end of clamp halves 22A and 22B, member 50 also holds fixation pin 20 in position with respect to rod 30.

FIG. 3 is an exploded view of FIG. 2. As noted, in the preferred embodiment, distal holes 302A and 302B in clamp halves 22A and 22B, respectively, receive distal bolt 31 by engagement of internal threads 301. Proximal holes 303A and 303B in clamp halves 22A and 22B receive shank 55 and threads 52 of member 50. Nut 61 secures member 50, thereby retaining fixation pin 20 inserted through hole 506 in shank 54 of member 50. As nut 61 is tightened, head 51 of member 50 is forced against washer 53 which is constructed with indentation divot 504 to grip pin 20. Surface 502 of washer 53 is advantageously rough to engage surface 304 on clamp half 22A to help prevent twisting of washer 53. As nut 61 continues to be tightened, circular pressure increases on fixation pin 20 by the effective reduction in the diameter of hole 506 in shank 54 of member 50, thereby securely grasping fixation pin 20 with little likelihood of longitudinal or rotational movement. At the same time, and in conjunction with bolt 31, clamp halves 22A and 22B lock onto rod 30 also preventing longitudinal and rotational movement.

Figure 4:
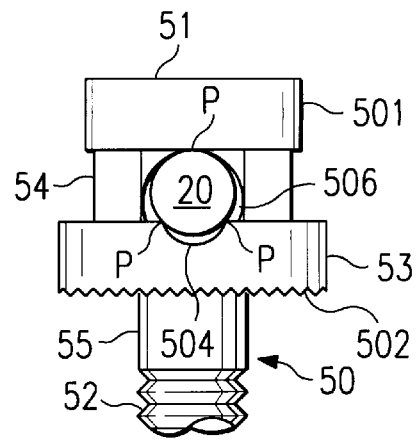
FIG. 4 is a detail of the three point grip on fixation pin 20.

FIG. 4 shows the retention of fixation pin 20 by member 50 in more detail. As seen on FIG. 4, hole 506 is oversized with respect to the diameter of pin 20 so that positive profile threads 21 may pass through hole 506. Oversized hole 506 also accommodates a range of diameters of pins 20 to be used and also allows pins 20 to be added to device 11 even after other pins 20 are in place and connected to bone 10A, 10B.

With further reference to FIG. 4, washer 53 provides a divot 504 engaging on the outer surface of pin 20. The profile of divot 504 is selected so as to ensure that three points of contact P are made in the retention of pin 20. These three points of contact P consist of two points of contact at the extremities of divot 504, and one point of contact on the inside of hole 506. The three points of contact P thus provide improved grip of pin 20 over, for example, the two points of contact that would be enabled if the profile of divot 506 was selected to be too wide or too shallow.

Figure 5A:
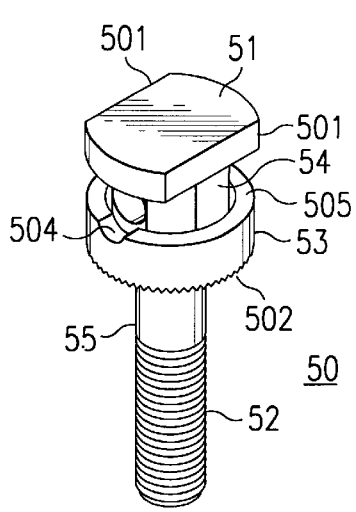
FIGS. 5A and 5B illustrate keying of toothed washer 53 and shank 54 to prevent relative rotation when assembled.
Figure 5B:
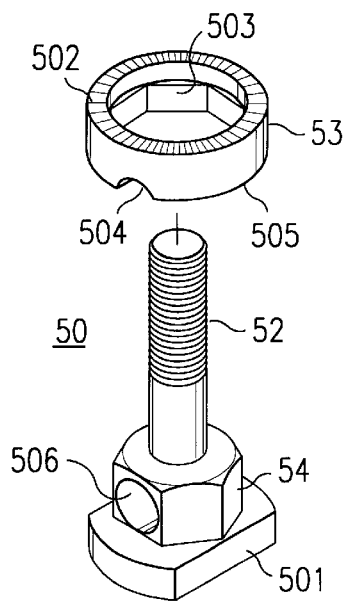

FIGS. 5A and 5B show shank 54 in member 50 to be hexagonal in profile, cooperating with the corresponding hexagonal internal profile 503 of washer 53, thereby preventing rotation of washer 53 when received onto shank 54 of member 50. Divot 504 in washer 53 may then be kept correctly aligned with hole 506 in shank 54 so as to consistently provide the three points of contact P on pin 20 described above with reference to FIG. 4. While a preferred embodiment as illustrated herein uses matching hexagonal shapes of shank 54 and internal profile 503 of washer 53 as a method of "keying," it will be appreciated that this method is exemplary only, and that other methods of keying to prevent rotation thereof with respect to shank 54 may be used with equivalent enabling effect.

As shown in FIG. 5B, in one embodiment washer 53 may be separable from member 50. Alternatively, as shown on FIG. 5A, in another embodiment washer 53 may be prevented from such complete separation by, for example, the flaring of shank 54 once washer 53 has been received thereon (flaring not illustrated).

With further reference to FIG. 3, and as discussed above, washer 53 advantageously also enables a non-slip interface with clamp half 22A. In a preferred embodiment, this non-slip interface is enabled via teeth 502 in the clamp side of washer 53 engaging optional corresponding notches 304 in clamp half 22A. Other non-slip engagements are possible (but not illustrated) to prevent unwanted rotation with respect to clamp halves 22A and 22B, such as a split spring lock washer, or a star or serrated lock washer (not illustrated).

FIG. 5A also shows head 51 of the bolt portion of member 50 with flattened sides 501. Advantageously, flattened sides 501 are aligned with the axis of hole 506. This arrangement permits a corresponding tool (not illustrated) to rotate the bolt, thereby to position fixation pin 20 about rod 30 before final securing with nut 61 (see FIG. 3). Flattened sides 501 also permit the optional use of a corresponding tool (not illustrated) to prevent transmission of torque to clamp assembly 200 or rod 30 during final tightening of nut 61. Again, the preferred embodiment's use of flattened sides 501 in bolt head 51 as a mechanism to enable rotational adjustment or decoupling torque is intended as exemplary only, and other mechanisms may be used with equivalent enabling effect, including indentations in the center of head 51, such as a Hex or Phillips opening, or various other engagement mechanisms.

As described briefly above, FIGS. 6A and 6B illustrate alternative embodiments for securing the distal end of clamp halves 22A and 22B to rod 30. In FIG. 6A, nut 62 secures distal bolt 31. Such an embodiment obviates the need for threads 301 as illustrated on FIG. 3. As shown on FIG. 6A, however, the height of nut 62 is advantageously selected so as not to interfere with pin 20 passing overhead. Alternatively, FIG. 6B illustrates use of rotational hinge 62 to enable securing of clamp halves 22A' and 22B' at the distal end with respect to clamp structure 200. The alternative embodiments illustrated in FIGS. 6A and 6B are not intended to be exhaustive, and other mechanisms may be used with equivalent enabling effect to secure the distal end of clamp halves 22A and 22B.

It will thus be appreciated that the inventive clamp assembly achieves the needs and objectives described earlier in this disclosure. Clamp halves 22A and 22B enable installation thereof on rod 30 without disturbing other clamp assemblies 200 already installed. Oversized hole 506 in shank 54 of member 50 enables fixation pins 20 with positive profile threads 21 to be inserted through hole 506 from the distal side and into bone 10A or 10B without disturbing other clamp assemblies 200 already installed. Three points of contact P, as shown on FIG. 4, enable improved grip and retention of fixation pin 20 in the correct position once fixation is complete. Similarly, a non-slip interface between washer 53 and clamp-half 22A (such as illustrated as teeth 502 engaging optional notches 304 in a preferred embodiment according to FIG. 2) improves grip and retention of fixation pin 20 in the correct position once fixation is complete.

Also note that bolt 31 can serve to begin the clamping process so as to hold the clamp in a relatively secure manner with respect to rod 30 until fixation pin can be permanently positioned in the fixation surface, such as bone 10A, 10B. This then also serves as a platform to stabilize the distal end of fixation pin 20 and to give a line of sight for proper placement of the pin.

Also, while a single fixation pin 20 is shown with respect to each securing device, the concept of the invention is not so limited, and more than one such fixation pin may be attached to the same securing device, for example, by adding second and even third shanks 54 (and holes 506) to member 50. Also, pins 20 can be added on the second side of member 50 by replacing bolt 31 with member 50.

Although the present invention and its advantages have been described in detail, it should be understood that various changes, substitutions and alterations can be made herein without departing from the spirit and scope of the invention as defined by the appended claims.

What is claimed is:

1. A device for clamping one or more fixation pins to a circular rod in a manner to prevent each pin from longitudinally or rotationally moving with respect to the rod, wherein said rod is positionable substantially parallel to a fixation surface, said device comprising:

a clamp securely positionable both rotatably and longitudinally to a rod, said clamp portion including securing means disposed on opposite surfaces of said rod for securely positioning both rotatably and longitudinally at least one said fixation pin;

at least one of said securing means including means for allowing said fixation pin to be attached to or removed from said fixation surface while other said fixation clamps remain attached to said fixation surface; and a mating threaded interface between said clamp and said rod, the mating threaded interface enabling said secure positioning both rotatably and longitudinally between said clamp and said rod.

2. The device of claim 1 wherein the fixation pin has positive threads for engagement with the fixation surface.

3. A device for clamping one or more fixation pins to a circular rod in a manner to prevent each pin from longitudinally or rotationally moving with respect to the rod, wherein said rod is positionable substantially parallel to a fixation surface, said device comprising:

a clamp securely positionable both rotatably and longitudinally to a rod, said clamp portion including securing means disposed on opposite surfaces of said rod for securely positioning both rotatably and longitudinally at least one said fixation pin;

at least one of said securing means including means for allowing said fixation pin to be attached to or removed from said fixation surface while other said fixation clamps remain attached to said fixation surface;

said allowing means including a bolt having a hole therethrough, said hole being larger than the diameter of a fixation pin to be secured thereby so that said fixation pin having a positive thread end can pass through said hole;

said allowing means further including a washer slidable along said bolt, the washer having a circular divot for frictionally engaging said fixation pin by decreasing the effective diameter of said hole when said bolt is drawn tight; and wherein said frictional engagement of said fixation pin in said hole is via at least three points of contact around the periphery of said fixation pin.

4. The device set forth in claim 3 further including:

a mating threaded interface between said clamp and said rod, the mating threaded interface enabling said secure positioning both rotatably and longitudinally between said clamp and said rod.

5. The device set forth in claim 3 wherein said washer and said bolt include a pair of mating surfaces for preventing rotation of said bolt and said washer with respect to each other so as to keep said divot lined up properly with said bolt hole.

6. A method of attaching one or more fixation pins to a fixation surface, said method comprising the steps of:

(a) positioning each section of a dual sectioned clamp on opposing surfaces of a circular rod, said positioning being at any place along said rod without regard to any other apparatus already positioned anywhere else along said rod, said clamp having a first portion extending beyond said rod proximally to said fixation surface and a second portion extending beyond said rod distally from said fixation surface, said clamp further having a semi-circular cutout in each said clamp section, said cutouts together surrounding said circular rod when said sections are in mating relationship;

(b) loosely inserting a first bolt through said first clamp portion, said first bolt including a hole therethrough;

(c) inserting and tightening a second bolt through said second clamp portion so as to frictionally lock said clamp at a selected attitude and position relative to said fixation surface;

(d) positioning said first bolt hole with respect to said fixation surface;

(e) sliding a fixation pin through said positioned bolt hole, said sliding being in a direction toward said fixation surface; and (f) subsequently tightening said first bolt so as to frictionally lock said fixation pin to said clamp.

7. The method of claim 6 wherein a mating threaded interface is formed between said semicircular cutouts and said circular rod when said sections are in a mating relationship.

8. The method of claim 6 wherein step (g) includes the substep of frictionally engaging said fixation pin to said bolt hole via at least three points of contact around the periphery of said fixation pin.

9. The method of claim 6 wherein step (g) includes the substep of reducing the diameter of said hole through which said fixation pin has been passed.

10. The method of claim 6 wherein said fixation pin includes positive threads on at least the end that passes through said bolt hole.

11. A bolt device for use in an external fixation device wherein the bolt device is used to position a circular fixation pin to a circular rod, said circular rod having positioned thereon a dual faced clamp extending outward on opposite peripheral surfaces of said rod, said outward extension each having means for maintaining said clamp frictionally engaged with said rod via a mating threaded interface, one of said maintaining means including said bolt device, said bolt device comprising:

a bolt having a head portion and a shaft portion extending perpendicular to said head portion, said shaft having threads at the distal end thereof;

said bolt shaft further comprising a shank portion wider than said shaft, said shank portion positioned in contact with a bottom surface of said head portion and running longitudinally down said shaft a short distance, said shank portion having therein a hole, said hole having a diameter large enough to accept the positive threads of a fixation pin;

said bolt device further comprising a washer having an inside diameter large enough to slide on said shank, said washer having a circular divot on a surface opposed to said bottom surface of said head, said washer keyed with said shank to prevent relative rotational displacement thereof, said washer further mating with said shank such that said divot is positioned to form a portion of the periphery of said shank hole such that when said bolt is tightened against said clamp, said washer slides along said shank, thereby reducing the effective size of said shank hole and frictionally engaging, via at least three points of contact, a fixation pin inserted through said hole; and said washer further disposed to frictionally engage said clamp via a non-slip interface.

12. A device for attaching one or more fixation pins to a fixation surface, said device comprising:

means for positioning each section of a dual sectioned clamp on opposing surfaces of a circular rod, said positioning being at any place along said rod without regard to any other apparatus already positioned anywhere else along said rod, said clamp having a first portion extending beyond said rod proximally to said fixation surface and a second portion extending beyond said rod distally from said fixation surface, said clamp further having a semicircular cutout in each said clamp section, said cutouts together adapted for surrounding said circular rod when said sections are in mating relationship;

a first bolt for insertion into said first clamp portion, said first bolt including a hole which can be positioned with respect to said fixation surface and through which a fixation pin can be inserted, said insertion being in a direction toward said fixation surface;

a second bolt for insertion into said second clamp portion, tightening of either of said first or second bolts being independently effective to secure said clamp to said circular rod; and means for frictionally locking said fixation pin within said hole.

13. The device of claim 12 wherein a mating threaded interface is formed between said semicircular cutouts and said circular rod when said sections are in mating relationship.

14. The device of claim 12 wherein said frictionally locking means includes means for tightening said first bolt without allowing said bolt hole to rotate with respect to said fixation surface.

15. The device of claim 12 wherein said frictional locking means includes means for frictionally engaging said fixation pin to said bolt hole via at least three points of contact around the periphery of said fixation pin.

16. The device of claim 12 wherein said frictionally locking means includes means for reducing the diameter of said hole through which said fixation pin has been inserted.

17. The device of claim 12 wherein said fixation pin includes positive threads on at least the end that passes through said bolt hole.

* * * * *